United States Patent

Baller et al.

[11] Patent Number: 5,566,243
[45] Date of Patent: Oct. 15, 1996

[54] METHOD AND APPARATUS FOR THE INSPECTION OF SURFACES

[75] Inventors: Wilfried Baller, Kirchseeon; Karl L. Schinner, Diessen Am Amme; Udo Kolb, München, all of Germany

[73] Assignee: Rheinmetall Sick Optical Inspection Systems GmbH, Munich, Germany

[21] Appl. No.: 247,984

[22] Filed: May 23, 1994

Related U.S. Application Data

[63] Continuation of Ser. No. 156,617, Nov. 23, 1993, abandoned.

[30] Foreign Application Priority Data

Nov. 24, 1992 [DE] Germany ............... 42 39 456.2

[51] Int. Cl.⁶ .................................... G06K 9/46
[52] U.S. Cl. ............... 382/108; 382/232; 382/272
[58] Field of Search ............... 382/1, 8, 65, 108, 382/272, 273, 232; 356/237, 371, 374; 348/86, 88, 102, 103

[56] References Cited

U.S. PATENT DOCUMENTS

| | | | |
|---|---|---|---|
| 4,519,041 | 5/1985 | Fant et al. | 382/54 |
| 4,700,398 | 10/1987 | Mizuno et al. | 382/1 |
| 4,752,897 | 6/1988 | Zoeller et al. | 382/16 |
| 5,078,496 | 1/1992 | Parker et al. | 356/371 |

FOREIGN PATENT DOCUMENTS

| | | |
|---|---|---|
| 0146005A2 | 6/1985 | European Pat. Off. . |
| 0271230A2 | 6/1988 | European Pat. Off. . |
| 0460431A1 | 12/1991 | European Pat. Off. . |

Primary Examiner—Leo Boudreau
Assistant Examiner—Chris Kelley
Attorney, Agent, or Firm—Spencer & Frank

[57] ABSTRACT

A method of inspecting the surfaces of materials to be examined, wherein the surface is scanned line by line by an optical measurement pickup and the signal furnished by the measurement pickup is processed in order to obtain information about the consistency of the surface of the material to be examined, with the picked up lines each being processed in sections in that for each section the average, the maximum and/or the minimum values, as well as an intermediate value, which is representative of the respective section and which is used for further processing, are determined. If the maximum or minimum values lie outside of a given tolerance zone that extends around the average value, the intermediate value equals the maximum or minimum, respectively, otherwise it equals the average value.

24 Claims, 1 Drawing Sheet

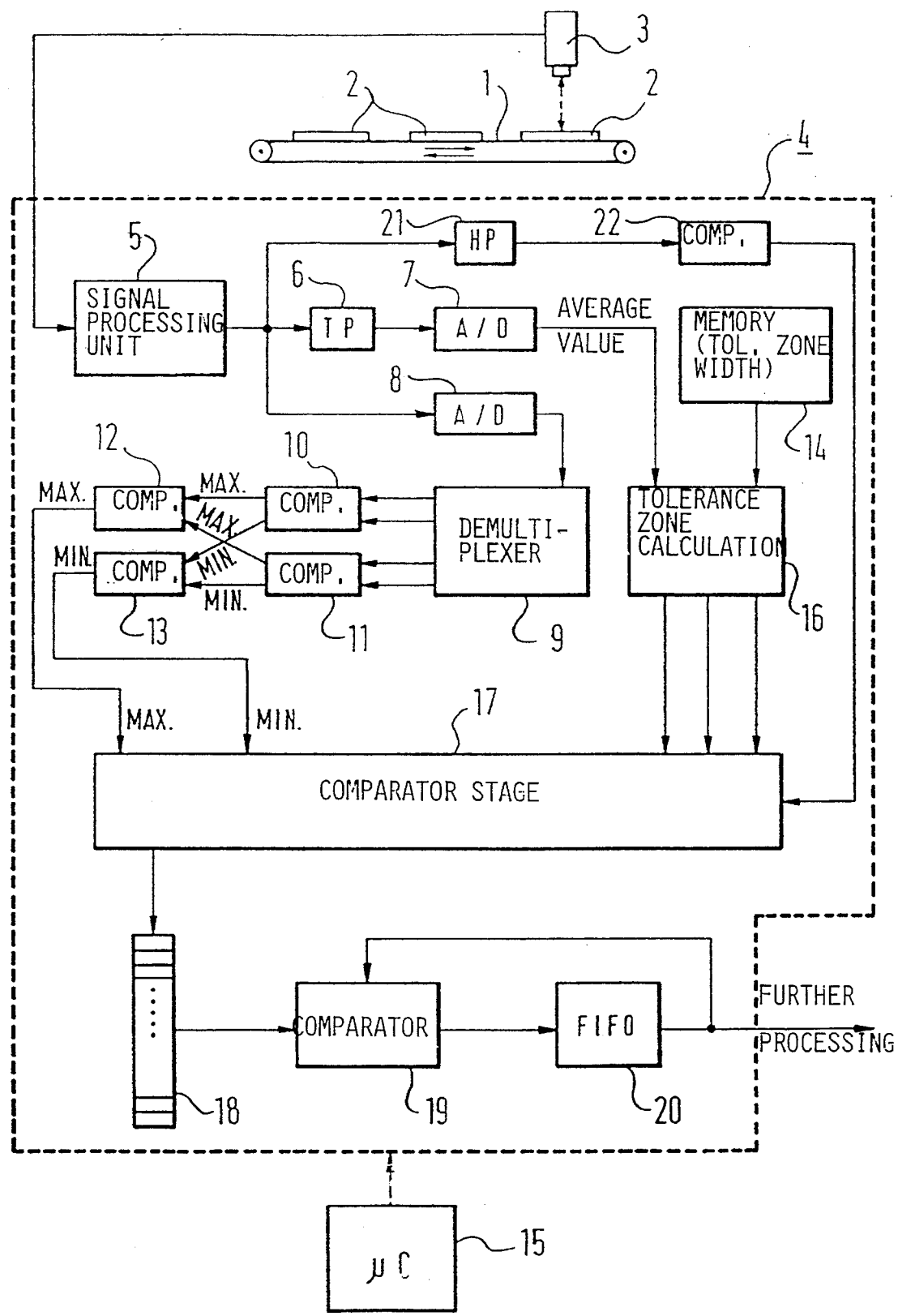

5,566,243

METHOD AND APPARATUS FOR THE INSPECTION OF SURFACES

CROSS REFERENCE TO RELATED APPLICATION

This is a continuation of U.S. patent application Ser. No. 08/156,617, filed Nov. 23, 1993, now abandoned.

This application claims the priority of German Patent Application No. P4,239,456.2 filed Nov. 24th, 1992, which is incorporated herein by reference.

BACKGROUND OF THE INVENTION

The present invention relates to a method of inspecting surfaces of materials to be examined wherein the surface is scanned line by line by means of an optical measurement pickup and the signal furnished by the measurement pickup is processed to provide information about the surface consistency of the material being examined.

The invention further relates to a surface inspection system including an optical measurement pickup, particularly a laser scanner or a video camera, which line by line scans the surface structure of a material to be examined, and a signal evaluation unit which processes the signal furnished by the measurement pickup.

Such methods and systems are used, for example, to detect surface flaws during the production or processing of metal, paper and textile panels. In these systems, for example, the material transported on a conveyor belt is moved past a measurement pickup which scans the surface of this material line by line, with this measurement pickup furnishing a signal that is representative of the material surface and is subsequently evaluated by a flaw detection unit.

In these systems, it is considered to be a drawback that they either operate with an insufficiently high resolution, so that the reliability of the systems is limited and thus reliable flaw detection cannot be ensured, or the resolution is high enough to ensure reliable flaw detection but this can be realized only at high manufacturing expense, and thus considerably reduce the economical utility of the system.

It may further be a problem to detect faulty patterns in the material surface that extend over a certain area since for this purpose, on the one hand, a number of scanned lines that cover the faulty pattern must be stored and, on the other hand, it must also be ensured that a subsequent association of the individual scanned lines with their position on the material surface to be examined must be possible. This poses problems, particularly if the material to be examined does not move past the measurement pickup at a constant speed.

SUMMARY OF THE INVENTION

It is an object of the present invention to provide a method of inspecting surfaces and a surface inspection system, respectively, with which small surface flaws can be detected with high probability and at low cost.

In particular, such a method and system are to make possible also the reliable detection of surface patterns or faulty patterns that extend over a region of the material surface that is covered by several scanned lines.

This is accomplished according to the method of the invention in that signals corresponding to the respective picked up lines are each processed in sections in that for each section an average value, the maximum value and/or the minimum value as well as an intermediate value, that is representative of the section and is used for further processing, are determined. For the case that the maximum or the minimum lies outside of a tolerance zone around the average value, the respective intermediate value is equal to the maximum or minimum, respectively; otherwise the respective intermediate value is equal to the average value.

The surface inspection system according to the invention solves the problem on which the invention is based in that the signal evaluation unit includes a preprocessing stage for data reduction in which the signal corresponding to the detected lines are each processed in sections in that for each section the average value, the maximum and/or the minimum value as well as an intermediate value, that is representative of the respective section and is used for further processing, are determined. For the case that the maximum or the minimum value lies outside of a tolerance zone around the average value, the determined intermediate value is equal to the maximum or minimum value, respectively, and otherwise is equal to the average value.

In a preferred embodiment of the method according to the invention, the analog signals furnished by the optical measurement pickup are converted to digital values, with each picked up line section having an associated given number of digital values. For example, two, four or more digital values may be determined for each line section.

From the digital values belonging to a line section, the respective average, maximum and minimum values can then be determined by a computer. From these values and the magnitude of the given tolerance zone, it is then possible to calculate the intermediate value representing the respective line section. Thus, only precisely one representative digital intermediate value is available for each line section which can then be further processed by a digital signal processing stage.

In an advantageous feature of the method according to the invention, the magnitude of the tolerance zone can be set to the respective requirements and environmental conditions. In this way it is possible, for example, to eliminate noise influences or interfering light effects from the signal furnished by the measurement pickup. In an advantageous manner, the tolerance zone may here also be set dynamically in that the magnitude of the tolerance zone is adapted to the magnitude of the noise signal that is superposed on the measurement signal in the section adjacent to the section presently being picked up.

In certain applications, it is desirable to detect surface patterns on the material surface being examined, with such patterns extending over several scanned lines. For this purpose, at least so many scanned lines must be examined and compared with one another during the signal evaluation that it is ensured that the surface pattern to be detected is completely covered by the jointly examined scanned lines. For this purpose, it is necessary to store the intermediate values of a corresponding number of scanned lines to thus be able to compare these values.

In a further preferred embodiment of the method according to the invention, the material to be examined is moved past the optical measurement pickup by means of an advancing device, for example a conveyor belt. The decisive factor here is the relative movement between the measurement pickup and the material to be examined. Consequently, it is also possible to keep the material to be examined stationary and move the measurement pickup past the material. The relative movement between the material to be examined and the measurement pickup is preferably perpendicular to the direction of a scanned line.

For the detection of surface patterns or faulty patterns, information must be available for signal evaluation indicating the location on the material being examined at which the marking significant for a surface pattern or a flaw that is a component of the faulty pattern is disposed. By storing the scanned lines, it is possible to easily determine at which position within the scanned line the marking or a flaw occurred.

With respect to the position perpendicular to the direction of the scanned lines, that is, for example in the direction of advancement, it is necessary during the signal evaluation to determine or keep constant the local spacing of two successive scanned lines. This information is obtained from the line scanning rate and the rate of advance. There is no problem if rate of advance and line scanning rate are constant since then a constant number of scanned lines is always determined during each unit of advancement and the determination of a flaw or a marker position relative to the direction of advance can be accomplished without difficulty.

In certain cases, however, it happens that, although the system operates with a constant line scanning frequency, the speed of advance cannot be kept constant or is intentionally varied. In such case, and according to a preferred feature of the method according to the invention, the position of a marker or a flaw in the direction of advancement can nevertheless be determined accurately in that the detected scanned lines are processed in a manner such that a given number of scanned lines per unit of advancement is constantly sent for further processing. This can be accomplished, for example, in that it is determined that precisely one scanned line is sent for further processing per unit of advancement corresponding to a certain length of the advancement path, with the first line picked up during a unit of advancement being stored. If further scanned lines follow within the same unit of advancement, these new lines overwrite the old line and finally, at the end of a unit of advancement, the scanned line presently stored in the memory is the one sent for further processing. In this way, it is always the last line picked up during one unit of advancement which is processed further.

It is also possible to store all scanned lines picked up during one period of advancement, to compare them with one another and to combine them according to a given algorithm into a single scanned line which is then used for further processing. For example, the first scanned line picked up during a unit of advancement could be stored and the algorithm could be designed such that the maxima or minima of this first stored line are overwritten by maxima or minima of a greater magnitude occurring at the respective line position of subsequent lines within the same unit of advancement. Likewise, stored average values are overwritten if at the corresponding position within a scanned line a maximum or minimum occurs in the next following line.

In one advantageous embodiment of the surface inspection system according to the invention, the preprocessing stage in which the signals representing the picked up lines are processed in sections is configured as a microprocessor controlled data processing unit, with the signals furnished by the optical measurement pickup passing through at least one A/D converter to then be fed to the preprocessing stage as digital signals.

Preferably, the preprocessing stage includes two A/D converters. The first A/D converter serves to pick up the average values of the individual line sections, with this A/D converter receiving the signal furnished by the measurement pickup by way of an average value forming lowpass filter. The scanning frequency of this first A/D converter is here selected so that the A/D converter is charged with precisely one clock pulse signal per picked up line section, thus producing precisely one average value per picked up line section at the output of this A/D converter.

The second A/D converter receives the signal furnished by the measurement pickup without the signal first passing through the lowpass filter connected to the input of the first A/D converter. This second A/D converter is clocked by at least the double, preferably the quadruple clock frequency of the first A/D converter, thus producing at its output at least two, and preferably four, digital values per picked up line section, with these digital values representing the signal furnished by the measurement pickup in one line section.

The clock frequency of the first A/D converter is preferably adapted to the processing clock of the signal processing stage which follows the preprocessing stage and is, in particular, 20 MHz.

The clock frequency of the second A/D converter is preferably four to six times the clock frequency of the first A/D converter, particularly 80 MHz.

The two A/D converters preferably each have a word width from 6 to 16 bits. The output values of both A/D converters belonging to a respective line section can then travel in parallel to the further processing stages, preferably by way of suitable memory elements.

From the signals furnished by the second A/D converter, the maximum and/or the minimum values can be determined for each line section under control of a microprocessor. Those values that lie between the maximum and the minimum need then no longer be considered during the further processing.

If the first, average forming A/D converter is employed, it is no longer necessary to make a computer determination of the average value from the digital values furnished by the second A/D converter for each line section, thus reducing the computation load on the microprocessor controlling the preprocessing stage.

The scanned values determined for one line section may be processed further in parallel, for example by means of a demultiplexer, in that all scanned values picked up by the second A/D converter within a line section are present in parallel at the output of this demultiplexer.

As already mentioned above, the method according to the invention is able to ensure that in each case only a constant number of scanned lines per unit of advancement are sent for further processing. For this purpose it is possible, for example, to combine several scanned lines picked up within one unit of advancement into a single scanned line that is forwarded for further processing.

For this purpose, an advantageous surface inspection system for implementing the mentioned method is equipped with an intermediate memory in which at least the intermediate values for two scanned lines determined by the preprocessing stage can be stored. The scanned value present in this intermediate value memory can then be combined, according to a given algorithm, into a single scanned line.

The mentioned algorithm may be configured, for example such that the first scanned line picked up during a unit of advancement is stored and the maxima and minima of this line are overwritten by maxima and minima of a greater amount at a corresponding line position of subsequent lines within the same unit of advancement. Stored average values are also overwritten if a maximum or minimum follows at the corresponding position in a scanned line during the following line.

In this calculation operation it is necessary to be able to recognize without difficulties whether the scanned value is a maximum or a minimum or the average of a line section. Preferably, an additional status bit is introduced for this reason for each intermediate value so as to indicate whether the associated intermediate value is an extreme value (maximum or minimum) or an average value.

Preferably, the surface inspection system according to the invention is provided with a unit for detecting dark spikes. This unit is composed of a highpass filter with a comparator connected to its output and serves to eliminate the measurement signal falsifying effects of dark spikes.

This unit is able to distinguish between dark spikes and flaw signals, for example on the basis of their characteristic frequency and/or their amplitude.

Preferably, the detection of a dark spike in principle only makes available for further processing the respective minimum and average values of picked up signals during the occurrence of dark spikes, while the maxima are discarded. This is appropriate since dark spikes, in principle, have positive amplitudes and consequently produce maxima in the course of the signal which maxima actually do not exist in the surface being examined and consequently must be eliminated, for example, in the manner described above.

As an alternative, it is also possible to reject the scanned values picked up during the occurrence of a dark spike and instead continue to make available for further processing the scanned values picked up already before the occurrence of the dark spikes.

The present invention will be described below with reference to the drawing FIGURE.

BRIEF DESCRIPTION OF THE DRAWING

The FIGURE is a block circuit diagram depicting a preferred embodiment of a surface inspection system according to the invention for carrying out the method according to the invention.

DETAILED DESCRIPTION OF THE PREFERRED EMBODIMENTS

On a conveyor belt 1, the material 2 to be examined is transported in the direction of the arrow past a measurement pickup 3, for example, in the form of a video camera or a laser scanner. Measurement pickup 3 covers or scans the surface structure of the material 2 to be examined line by line, preferably perpendicular to the scanning direction, and furnishes a corresponding signal to a preprocessing stage 4 that is controlled by a microcomputer 15 and is a component of a signal evaluation unit (not shown here).

Preprocessing stage 4 serves to reduce the number or amount of data so that the components of the signal evaluation unit following preprocessing stage 4 and serving to detect possibly occurring surface flaws need process only a smaller data quantity, thus permitting greater operating speeds and a more economical manufacture of the signal evaluation unit.

The signal from measurement pickup 3 reaching preprocessing stage 4 is initially fed to a signal processing unit 5 which includes, for example, filter and amplifier stages. The thus processed signal of measurement pickup 3 is then processed further scanned line by scanned line, and in sections within each line. The object of this further processing is to combine the values picked up during one line section into a single measured value.

For this purpose, the processed signal is fed to an average forming lowpass filter 6 whose fundamental frequency is set such that an average value is present at its output which represents the average value of a line section. This average value is then fed to a first A/D converter 7 whose clock frequency is selected such that it is charged with precisely one clock signal during the picking up of a single line section. Thus, the respective digital average of a detected line section is present at the output of A/D converter 7.

The signal furnished by signal processing unit 5 is also fed to a second A/D converter 8 whose clock frequency is in the illustrated embodiment, four times the clock frequency of A/D converter 7. Thus, a serial sequence of digital values is present at the output of A/D converter 8 and represents the course of the signal furnished by measurement pickup 3.

In the illustrated preferred embodiment of the invention where each line is divided into four line sections, a group of four successive values furnished serially by A/D converter 8 are fed to a demultiplexer 9, with these four digital values then being available in parallel at the four outputs of the demultiplexer 9 and with each of these four values being representative of a line section. Two output values from demultiplexer 9 are fed to each one of two comparator stages 10 and 11 which determine which one of the two values it has received is the greater value and which is the lesser.

The greater of the values fed to comparator stage 10 and the greater of the values fed to comparator stage 11 are subsequently fed to a further comparator stage 12 which again determines the maximum from these two values and makes it available for further processing.

The lesser of the values fed to comparator stage 10 and the lesser of the values fed to comparator stage 11 subsequently are fed to a further comparator stage 13 which again determines the minimum from these two values and makes it available for further processing. Thus, the maximum of the scanned values determined by A/D converter 8 for each line section is present at the output of comparator stage 12, and the minimum of the scanned values determined by A/D converter 8 for each line section is present at the output of comparator stage 13.

The preprocessing stage 4 further includes a memory element 14 in which the width of the tolerance zone is stored. This stored value can be varied by microcomputer 15 as required. The output signal of memory 14 is fed together with the average value of a line section, as determined by A/D converter 7, to a stage 16 for calculating tolerance zones. In stage 16, the sum, on the one hand, and the difference, on the other hand, of the average value and the tolerance zone width are formed. Accordingly, the average value, the sum of the average value and the tolerance zone width, as well as the difference between the average value and the tolerance zone width are present at the three respective outputs of stage 16.

These three respective values from stage 16, the maximum value determined by comparator stage 12 and the minimum value determined by comparator stage 13 are fed together to a further comparator stage 17. From the values it receives, comparator stage 17 determines an intermediate value for each line section, with the intermediate value being equal to the maximum or the minimum, respectively, if the maximum or the minimum is greater or less, respectively, than the sum of the average value and the tolerance zone width or the difference between the average value and the tolerance zone width, respectively, and otherwise being equal to the average value. The intermediate value determined by comparator stage 17 is then fed to a line memory 18 which stores all intermediate values formed for each scanned line and makes them available in parallel for further processing.

Thanks to the unit following line memory 18 and composed of a comparator 19 and a FIFO memory 20, it is ensured that in each case only one scanned line per unit of advancement is able to reach the output of preprocessing stage 4 for further processing. This unit 19, 20 may be operated by the microcomputer 15 in various ways.

On the one hand, it is possible to send the scanned lines from line memory 18 without any change in comparator 19 to FIFO memory 20, with FIFO memory 20 applying a scanned line to the output of preprocessing stage 4 only if a unit of advancement is completed. In this way, the scanned line determined last during a unit of advancement always reaches the output of preprocessing unit 4.

It is also possible to operate unit 19, 20 in the following manner:

A first scanned line, determined during a unit of advancement, is fed without change to FIFO memory 20. The second line following this first line within the same unit of advancement is then compared with the first line in comparator 19. Then those values of the first line in FIFO memory 20 are overwritten by the values lying at the corresponding line position in the second line if a maximum or minimum of the second scanned line is greater or less, respectively, than the maximum or minimum, respectively, of the first scanned line or if an extreme value (maximum or minimum) of the second line follows an average value in the first line at the corresponding line position. Thus, an intermediate value combination from the first and second scanned lines is obtained in FIFO memory 20.

A third scanned line following the second line within the same unit of advancement is compared in succession in comparator 19 with the combination of the first and second lines already in FIFO memory 20, with these stored values of the combination of the first and second lines again being overwritten according to the above rule with the values of the third line. Thus a combination of the first, second and third lines is obtained in the FIFO memory 20. This process can be repeated until all scanned lines picked up during one unit of advancement have been processed. At the end of a unit of advancement, the combination of the processed scanned lines present in FIFO memory 20 is fed to the output of preprocessing stage 4.

The signal furnished by signal processing unit 5 also is fed to a unit for detecting dark spikes. This unit is composed of a highpass filter 21 with a comparator 22 connected to its output. Dark spikes are identified in this unit due to their amplitude and frequency and, if a dark spike is present, comparator 22 feeds an appropriate signal to comparator stage 17.

If a dark spike is detected, comparator stage 17 makes available for further processing, in principle, only the minima and average values, respectively, picked up during the occurrence of the dark spike, while the maxima are discarded. Alternatively, the comparator stage 17 can disregard the scanned values received during the occurrence of a detected dark spike and instead make available the values picked up prior to the occurrence of the dark spike. In this way, measurement signal falsifying effects of dark spikes can be eliminated.

It will be understood that the above description of the present invention is susceptible to various modifications, changes and adaptations, and the same are intended to be comprehended within the meaning and range of equivalents of the appended claims.

What is claimed is:

1. A method of inspecting a surface of materials to be examined in order to provide information about consistency of the surface of the material to be examined comprising the steps of scanning the surface line by line with an optical measurement pickup, and processing an output signal furnished by the measurement pickup line by line with each line being divided into sections and including: determining the average value, the maximum value and the minimum value for each said section, producing an intermediate value, which is representative of the section and which is used for further processing, from said determined maximum, minimum and average valuesfor the respective section, with said intermediate value being equal to said maximum value or said minimum value, respectively, if said maximum value or said minimum value, respectively, lies outside of a given tolerance zone that extends around said average value, and otherwise being equal to said average value.

2. A method as defined in claim 1, further comprising converting the picked up measurement values to digital values, with at least two digital values being determined for each line section from which said average, said maximum, and said minimum values for a respective line section are calculated in digital form, and with said intermediate value for a respective line section being calculated from the respective said digital average, maximum, and minimum values and said tolerance zone.

3. A method as defined in claim 2, wherein four digital values are determined for each line section.

4. A method as defined in claim 1, further comprising adjusting said tolerance zone according to respective requirements as a function of a noise signal superposed on the measurement signal in sections adjacent to the presently picked up section.

5. A method as defined in claim 1, further comprising storing said intermediate values of at least two scanned lines.

6. A method as defined in claim 1, further comprising moving the material to be examined and the measurement pickup past and relative to one another.

7. A method as defined in claim 6, wherein said step of scanning comprises scanning with a constant line scanning frequency, and said step of moving includes advancing the material to be examined and the measurement pickup past and relative to one another at an inconstant rate of advancement so that a correspondingly inconstant number of scanned lines per unit of advancement corresponding to a certain length of an advancement path are picked up; and further comprising processing said intermediate values for said scanned lines picked up during one unit of advancement such that a given number of scanned lines per unit of advancement is constantly furnished for further processing.

8. A method as defined in claim 7, wherein the scanned line picked up last during a unit of advancement is used for further processing.

9. A method as defined in claim 7, wherein the scanned lines picked up during one unit of advancement are compared with one another and are combined into a single line.

10. A method as defined in claim 9, wherein the first scanned line picked up during a unit of advancement is stored, the maxima or minima, respectively, of this line are overwritten by maxima or minima, respectively, that have a greater amount and lie at corresponding line positions of the next lines following within the same unit of advancement, and stored average values from the first line are overwritten by extreme values lying at corresponding line positions in the next following lines within the same unit of advancement.

11. In a surface inspection system for inspecting a surface of materials to be examined in order to provide information about consistency of the surface of the material to be examined, wherein the system includes an optical measurement pickup, particularly a laser scanner or a video camera, which covers the surface structure of a material to be examined line by line, and a signal evaluation unit which processes signals furnished by said measurement pickup; the improvement wherein said signal evaluation unit includes a preprocessing stage for data reduction which processes each signal corresponding to a picked up line furnished by said measurement pickup in sections in that for each section, the average, the maximum and the minimum values as well as an intermediate value, that is representative of the respective section and is used for further processing, are determined, with said intermediate value being equal to the maximum or the minimum value, respectively, if the maximum or the minimum value, respectively, lies outside of a given tolerance zone extending around the respective average value, and otherwise being equal to the respective average value.

12. A surface inspection system as defined in claim 11, wherein said preprocessing stage is a microprocessor controlled data processing unit.

13. A surface inspection system as defined in claim 11, wherein said preprocessing stage includes: a first A/D converter which receives the signal furnished by the measurement pickup via an average forming lowpass filter, with the clock frequency of said first A/D converter being such that a respective line section is picked up during a single clock pulse period; a second A/D converter which converts the signal furnished by the measurement sensor at at least double the clock frequency of said first A/D converter; and a digital data processing stage for determining the intermediate values and to which the output signals of both of said first and second A/D converters are fed.

14. A surface inspection system as defined in claim 13, wherein said digital data process of said preprocessing stage determines the maximum and the minimum values from the scanned values furnished by said second A/D converter for each respective line section.

15. A surface inspection system as defined in claim 13, wherein the clock frequency of said second A/D converter is four to six times as high as the clock frequency of said first A/D converter with the clock frequency of said first A/D converter being adapted to the processing clock pulse of a signal processing stage that follows said preprocessing stage.

16. A surface inspection system as defined in claim 13, wherein both of said first and second A/D converters have a word width of 6 to 16 bits.

17. A surface inspection system as defined in claim 16, wherein at least one additional bit in each intermediate value indicates whether the respective intermediate value is a maximum value, a minimum value or the average value of a respective line section.

18. A surface inspection system as defined in claim 13, wherein said digital data process stage of said preprocessing stage further includes a demultiplexer connected to the output of said second A/D converter and whose outputs furnish in parallel, for further processing, all scanned values fed to said second A/D converter within one line section.

19. A surface inspection system as defined in claim 18, wherein said digital data processing stage of each preprocessing stage further includes: a first comparator circuit which is connected to receive the output signals of said demultiplexer and which determines the respective maximum and minimum values of a line section, a tolerance zone circuit which is responsive to the average value produced by said first A/D converter to provide output values corresponding to the relationship of the average value and a desired tolerance zone; and a second comparator which receives the maximum and minimum values from said first comparator circuit and the output values of said tolerance zone circuit, and which produces the respective, intermediate values.

20. A surface inspection system as defined in claim 11, wherein said preprocessing stage further includes an intermediate value memory in which at least intermediate values of two scanned lines as determined by said preprocessing stage can be stored.

21. A surface inspection system as defined in claim 11, further comprising an advancing device which moves the material to be examined and said measurement pickup relatively past one another.

22. A surface inspection system as defined in claim 11, wherein said preprocessing stage includes a unit for detecting dark spikes, and composed of a highpass filter with a comparator connected to its output, to which the measurement signal from said optical measurement pickup is applied and which provides an output signal which eliminates falsifying effects of dark spikes in the measurement signal.

23. A method of operating a surface inspection system as defined in claim 22, comprising during the occurrence of a dark spike in the measurement signal, making available for further processing only the minimum and average values of the signals corresponding respective sections while discarding the respective maximum values.

24. A method of operating a surface inspection system as defined in claim 22, comprising: during the occurrence of a dark spike in the measurement signal, discarding the scanned values of the measurement signal picked up during the occurrence of a dark spike and instead making available for further processing the scanned values picked up already before the occurrence of the dark spike.

* * * * *